(12) United States Patent
Troetzschel et al.

(10) Patent No.: US 8,929,987 B2
(45) Date of Patent: Jan. 6, 2015

(54) ELECTRICAL BUSHING FOR AN IMPLANTABLE MEDICAL DEVICE

(75) Inventors: Jens Troetzschel, Bruchkoebel (DE); Heiko Specht, Hanau (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 368 days.

(21) Appl. No.: 12/850,412

(22) Filed: Aug. 4, 2010

(65) Prior Publication Data

US 2011/0034966 A1 Feb. 10, 2011

(30) Foreign Application Priority Data

Aug. 4, 2009 (DE) .......................... 10 2009 035 971

(51) Int. Cl.
*A61N 1/37* (2006.01)
*A61N 1/375* (2006.01)

(52) U.S. Cl.
CPC ................................... *A61N 1/3754* (2013.01)
USPC .......................................................... 607/37

(58) Field of Classification Search
USPC ..................................... 607/36–37
See application file for complete search history.

(56) References Cited

U.S. PATENT DOCUMENTS

| | | | |
|---|---|---|---|
| 4,352,951 A | 10/1982 | Kyle | |
| 4,362,792 A | 12/1982 | Bowsky et al. | |
| 4,456,786 A | 6/1984 | Kyle | |
| 4,488,673 A * | 12/1984 | Hopper, Jr. | 228/122.1 |
| 4,678,868 A | 7/1987 | Kraska et al. | |
| 4,737,601 A | 4/1988 | Gartzke | |
| 4,774,953 A | 10/1988 | Foote | |
| 4,816,621 A | 3/1989 | Huebner et al. | |
| 4,991,582 A | 2/1991 | Byers et al. | |
| 4,992,910 A | 2/1991 | Evans | |
| 5,046,262 A | 9/1991 | Kerbaugh | |
| 5,245,999 A | 9/1993 | Dahlberg et al. | |
| 5,272,283 A | 12/1993 | Kuzma | |
| 5,513,793 A | 5/1996 | Malmgren | |
| 5,654,106 A | 8/1997 | Purnell et al. | |
| 5,683,435 A | 11/1997 | Truex et al. | |
| 5,738,270 A | 4/1998 | Malmgren | |
| 5,750,926 A | 5/1998 | Schulman et al. | |

(Continued)

FOREIGN PATENT DOCUMENTS

| | | |
|---|---|---|
| DE | 69729719 | 7/2005 |
| DE | 102009035971 | 2/2011 |
| DE | 102009035972 | 4/2011 |

OTHER PUBLICATIONS

Office Action for U.S. Appl. No. 12/850,406 mailed Sep. 17, 2012 (11 pages).

(Continued)

*Primary Examiner* — Paula J Stice
(74) *Attorney, Agent, or Firm* — Dicke, Billig & Czaja, PLLC

(57) ABSTRACT

One aspect relates to an electrical bushing for an implantable medical device, having an annulus-like holding element for holding the electrical bushing in the implantable medical device, whereby the holding element includes a through-opening, at least one elongated conducting wire extends through the through-opening, and an insulation element for forming a hermetic seal between the holding element and the conducting wire is arranged in the through-opening. One aspect provides for a cermet-containing bearing element to be arranged between the insulation element and the conducting wire.

10 Claims, 2 Drawing Sheets

(56) References Cited

U.S. PATENT DOCUMENTS

| | | |
|---|---|---|
| 5,769,874 A | 6/1998 | Dahlberg |
| 5,782,891 A | 7/1998 | Hassler et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 6,232,004 B1 | 5/2001 | Lasater |
| 6,284,080 B1 | 9/2001 | Haq et al. |
| 6,414,835 B1 | 7/2002 | Wolf et al. |
| 6,579,492 B2 | 6/2003 | Wehler |
| 6,586,675 B1 | 7/2003 | Bealka et al. |
| 6,660,116 B2 | 12/2003 | Wolf et al. |
| 7,068,491 B1 | 6/2006 | Burdon et al. |
| 7,107,099 B1 | 9/2006 | O'Phelan et al. |
| 7,222,419 B2 | 5/2007 | Horng et al. |
| 7,480,988 B2 | 1/2009 | Ok et al. |
| 7,569,452 B2 | 8/2009 | Fu et al. |
| 7,668,597 B2 * | 2/2010 | Engmark et al. .............. 607/37 |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 8,000,804 B1 * | 8/2011 | Wessendorf et al. ......... 607/116 |
| 8,155,743 B2 | 4/2012 | Rundle et al. |
| 8,163,397 B2 | 4/2012 | Ok et al. |
| 8,189,333 B2 | 5/2012 | Foster |
| 8,494,635 B2 | 7/2013 | Troetzschel et al. |
| 8,528,201 B2 | 9/2013 | Troetzschel et al. |
| 2001/0018012 A1 * | 8/2001 | Harmand et al. .............. 408/1 R |
| 2002/0166739 A1 * | 11/2002 | Naerheim ................. 188/251 R |
| 2003/0109903 A1 | 6/2003 | Berrang et al. |
| 2004/0023101 A1 * | 2/2004 | Jacobson et al. ............... 429/38 |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2007/0041164 A1 | 2/2007 | Greenberg et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2009/0281586 A1 | 11/2009 | Lim |
| 2010/0121438 A1 | 5/2010 | Jarvik |
| 2011/0032658 A1 | 2/2011 | Iyer |
| 2011/0034965 A1 | 2/2011 | Troetzschel et al. |
| 2011/0048770 A1 | 3/2011 | Reiterer et al. |
| 2011/0094768 A1 | 4/2011 | Davis et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2013/0299233 A1 | 11/2013 | Troetzschel et al. |
| 2014/0008121 A1 | 1/2014 | Troetzschel et al. |

OTHER PUBLICATIONS

Final Office Action for U.S. Appl. No. 12/850,406 mailed Feb. 25, 2013 (16 pages).

Restriction Requirement for U.S. Appl. No. 13/018,882 mailed Dec. 20, 2012 (5 pages).

Notice of Allowance for U.S. Appl. No. 13/018,882 mailed May 10, 2013 (25 pages).

Office Action for U.S. Appl. No. 13/018,847 mailed Dec. 5, 2012 (24 pages).

Notice of Allowance for U.S. Appl. No. 13/018,847 mailed Mar. 25, 2013 (25 pages).

Office Action for U.S. Appl. No. 12/850,406 mailed Sep. 12, 2013 (16 pages).

A PDF Dictionary definition of cermet found at The Free Dictionary site http://www.thefreedictionary.com/cermets.

Notice of Allowance for U.S. Appl. No. 12/850,406 mailed Feb. 5, 2014 (9 pages).

Notice of Allowability for U.S. Appl. No. 13/018,882 mailed Jul. 16, 2013 (6 pages).

Office Action for U.S. Appl. No. 13/942,685 mailed Dec. 23, 2013 (10 pages).

Final Office Action for U.S. Appl. No. 13/942,685 mailed Apr. 14, 2014 (22 pages).

* cited by examiner

ELECTRICAL BUSHING FOR AN IMPLANTABLE MEDICAL DEVICE

CROSS-REFERENCE TO RELATED APPLICATIONS

This Utility patent application claims priority to German Patent Application No. DE 10 2009 035 971.0, filed on Aug. 4, 2009, which is incorporated herein by reference. This patent application is also related to Utility patent application filed on even date herewith, entitled "CERMET-CONTAINING BUSHING FOR AN IMPLANTABLE MEDICAL DEVICE" having Ser. No. 12/850,406, which is incorporated herein by reference.

BACKGROUND

One aspect relates to an electrical bushing for an implantable medical device having an annulus-like holding element for holding the electrical bushing in the implantable medical device, whereby the holding element includes a through-opening, at least one elongated conducting wire extends through the through-opening, an insulation element for forming a hermetic seal between the holding element and the conducting wire is arranged in the through-opening. One aspect relates to a method for producing an electrical bushing for an implantable medical device.

DE 697 297 19 T2 describes an electrical bushing for an implantable electrical therapeutic device. Electrical bushings of this type serve to establish an electrical connection between a hermetically sealed interior and an exterior of said therapeutic device. Known implantable therapeutic devices include cardiac pacemakers or defibrillators, which usually include a hermetically sealed metal housing, which is provided with a connection body, also called header, on one side. Said connection body includes a connection socket for connecting electrode leads. In this context, the connection socket includes electrical contacts that serve to electrically connect electrode leads to the control electronics in the interior of the housing of the implantable therapeutic device—also called implantable device. An essential prerequisite for an electrical bushing of this type is hermetic sealing with respect to the surroundings.

Accordingly, it needs to be made sure that the conducting wires that are introduced into an insulation element and via which the electrical signals proceed, are introduced into the insulation element without any gaps. In this context, it has proven to be disadvantageous that the conducting wires in general are made of a metal and need to be introduced into a ceramic insulation element. In order to ensure long-lasting connection between the two elements, the internal surface of the bore hole in the insulation element must be metallized for soldering the conducting wires into them. Said metallization inside the bore hole in the insulation element has proven to be difficult to apply. Homogeneous metallization of the internal surface of the bore hole in the insulation element can be ensured only by means of expensive procedures.

For these and other reasons there is a need for the present invention.

SUMMARY

One aspect is an electrical bushing for an implantable medical device, having an annulus-like holding element for holding the electrical bushing in the implantable medical device. The holding element includes a through-opening. At least one elongated conducting wire extends through the through-opening and an insulation element for forming a hermetic seal between the holding element and the conducting wire is arranged in the through-opening. A cermet-containing bearing element is arranged between the insulation element and the conducting wire.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
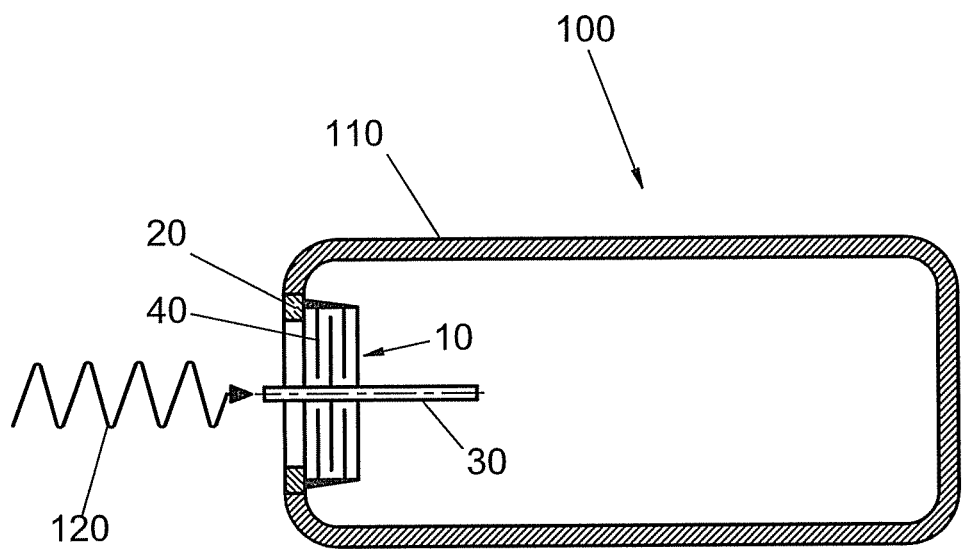
FIG. 1 illustrates an implantable medical device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One aspect creates an electrical bushing for an implantable medical device, in which the aforementioned disadvantages are avoided, and in which a long-lasting sealing connection between insulation element and conducting wire is ensured. One aspect is an implantable medical device and one aspect is a method for producing an electrical bushing for an implantable medical device. Any features and details that are described in this context in relation to the electrical bushing or the implantable medical device shall also apply in relation to the method, and vice versa.

The electrical bushing according to one embodiment is characterized in that a cermet-containing bearing element is arranged between the insulation element and the conducting wire.

One embodiment is based on the utilization of the special properties of a cermet. Since the cermet, on the one hand, is a composite material made of a ceramic material in a metallic matrix, the cermet-containing bearing element is easy to introduce into the insulation element, which consists of a ceramic material. On the other hand, the elongated conducting wire is easy to connect to the metallic matrix of the cermet. Accordingly, the cermet-containing bearing element is a simple, biocompatible, long-lasting connecting bridge between the insulation element and the conducting wire.

In the context of one embodiment, the terms, "cermet" or "cermet-containing", shall refer to all composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or the cermet-containing bearing element proceeds just like with homogeneous powders with the exception that the metal is compacted more strongly than the ceramic material at the same pressuring force. The cermet-containing bearing element has a higher thermal shock and oxidation resistance than sintered hard metals. In most cases, the ceramic components of the cermet are aluminum oxide ($Al_2O_3$) and zirconium dioxide ($ZrO_2$), whereas niobium, molybdenum, titanium, cobalt, zirconium, chromium are conceivable as metallic components.

In the context of one embodiment, the term, "cermet-containing", refers to a mixture of materials in which at least one part of the material of the bearing element and/or the fringe is a cermet. It can be formed and fired from a cermet-containing material and/or powder. This scope also encompasses a development, in which the bearing element and/or the fringe consist of a cermet. In this variant, the corresponding element—the bearing element and/or the fringe—are completely made of a cermet.

In order to ensure homogeneous connection between the conducting wire and the bearing element, it has proven to be advantageous for the bearing element to separate the conducting wire from the insulation element in a cuff-like manner. The bearing element can be designed to be tubular in shape and has a length that corresponds to the height of the insulation element. This ensures that no direct connection occurs between the conducting wire and the insulation element. Rather, the bearing element separates the conducting wire from the insulation element along its entire path through the insulation element. This arrangement provides that no fissures or gaps can arise between the conducting wire and the insulation element.

Another development of the electrical bushing is characterized in that a cermet-containing fringe is arranged between the insulation element and the holding element. As shall be explained in more detail below, the holding element is often made of a metal. Accordingly, connecting the ceramic insulation element to the metallic holding element may result in similar disadvantages as have been illustrated above for the conducting wire. According to one embodiment, it is envisioned to utilize the properties of a cermet in this context as well. Accordingly, the insulation element is surrounded by a cermet-containing fringe in an annulus-like manner. The cermet-containing fringe ensures that no gaps or fissures arise between the holding element and the insulation element, and facilitates easy and inexpensive connection of the metallic holding element to the ceramic insulation element. In one embodiment, the cermet-containing fringe surrounds the insulation element in the form of a film and/or collar, and surrounds it completely. This ensures that there is no direct contact between the insulation element and the holding element which might give rise to imperfect sealing.

One development of the electrical bushing is characterized in that the at least one elongated conducting wire includes a metal from the group of titanium (Ti), tantalum (Ta), platinum (Pt) or an alloy of at least one of said metals. Also conceivable as further metals for the elongated conducting wire, which are also biocompatible and corrosion-resistant, are iridium, niobium or a tantalum-niobium-tungsten alloy (containing 10 wt % niobium and 7.5 wt % tungsten). Conducting designed as described have the desired biocompatibility, are corrosion-resistant, and can be connected reliably to the cermet-containing bearing element according to one embodiment.

An embodiment includes an insulation element that is made from an insulating composition of materials. The insulation element serves to electrically insulate the conducting wire from the holding element and any other objects of the implantable medical device. Electrical signals proceeding through the conducting wire are not to be attenuated or short-circuited by contacting the housing of the implantable device. In addition, though, the insulation element must include a biocompatible composition in order to be implanted medically. For this reason, it is preferred in one embodiment for the insulation element to consist of a glass-ceramic or glass-like material. It has proven to be preferred in one embodiment for the insulating composition of materials of the insulation element to be at least one from the group of aluminum oxide ($Al_2O_3$), magnesium oxide (MgO), zirconium oxide ($ZrO_2$), aluminum-titanate ($Al_2TiO_5$), and piezo-ceramics. The aluminum oxide ceramic material has a high electrical resistance and low dielectric losses. Moreover, these properties are supplemented by the high thermal resistance as well as good biocompatibility.

Another development of the bushing according to one embodiment is characterized in that the holding element includes at least one flange, whereby, for example, the flange is conductive like a metal. The flange serves to seal the electrical bushing with respect to a housing of the implantable device. The holding element holds the electrical bushing in the implantable device. In the development described at present, the holding element includes at least one flange on an external surface. Said flanges form a bearing, which can be engaged by the lids of the implantable medical device, and in one embodiment, can be engaged in a sealing manner. Accordingly, the holding element with flanges attached to it can have a U- or H-shaped cross-section. Integrating at least one flange into the holding element ensures safe, impact-proof, and long-lasting integration of the electrical bushing into the implantable device. In addition, the flanges can be designed such that the lids of the implantable device are connected to the holding element in a non-positive fit- and/or positive fit-like manner.

An embodiment is characterized in that the holding element and/or the at least one flange include(s) a metal from the group, titanium (Ti), tantalum (Ta), iridium (Ir), niobium (Nb) or platinum (Pt) or an alloy of at least one of said metals. As explained above, the holding element and/or the flange is/are in direct contact to the housing of the implantable medical device. Both the holding element and the flange must not corrode and must have a desired biocompatibility since the implantable device is to be introduced into a human body. For this reason, the metals specified above have proven to be advantageous in some embodiments. In addition, they can be connected to the cermet of the fringe easily and in a long-lasting manner.

The scope of one embodiment also includes use of a cermet-containing bearing element between an insulation element and a conducting wire in an electrical bushing for an implantable medical device. In this context, any features and details that were described in relation to the electrical bushing and/or the method shall obviously also apply in relation to the use of the cermet-containing bearing element.

Another embodiment is an implantable medical device, for example, a cardiac pacemaker or defibrillator, having an electrical bushing according to any one of the claims described above.

One embodiment also relates to a method for producing an electrical bushing for an implantable medical device. The disadvantages arising during the production of electrical bushings of this type have been described above. The objective resulting therefrom has also been specified above. According to one embodiment, the method for producing an electrical bushing for an implantable medical device includes the following steps:

a. generating an insulation element green compact for an insulation element from an insulating composition of materials;

b. forming at least one cermet-containing bearing element green compact for a bearing element;

c. introducing the at least one bearing element green compact into the insulation element green compact;

d. firing the insulation element green compact and the at least one bearing element green compact to obtain an insulation element with at least one bearing element;

e. inserting an elongated conducting wire into the at least one bearing element; and f. surrounding the insulation element, at least in part, with a holding element.

Any features and details in this context that are described in relation to the electrical bushing shall obviously also apply in relation to the method according to one embodiment, and vice versa. The special feature of the method according to one embodiment results from both the insulation element and the bearing element comprising ceramic components which are processed by means of a sintering procedure. According to procedural step a), an insulation element green compact is formed from an insulating composition of materials. The insulating composition of materials is a powder mass whose powder particles illustrate at least a minimum of cohesion. This is commonly effected in that a grain size of the powder particles does not exceed 0.5 mm. In this context, the production of a green compact is effected either by pressing powder masses or by forming and subsequent drying. According to step b), a cermet-containing bearing element green compact is then generated in parallel or subsequently.

One embodiment provides the two green compacts to be placed together and fired thereafter. Firing—also called sintering—is understood to mean a heat treatment below the melting temperature of the powder particles of the green compact. In the process, the porosity and the volume of the green compact are decreased markedly. Accordingly, the special feature of one embodiment is that the green compact of the bearing element and the green compact of the insulation element are fired jointly in one step. An insertion of the elongated conducting wire into the conduction element can follow thereafter. The contacting between the bearing element and the conducting wire is effected by soldering or welding, whereby, for example, laser welding or resistance welding have proven to be preferred in some embodiments.

One development of the method according to one embodiment is characterized in that step a) includes a partial sintering of the insulation element green compact. As part of said only partial sintering, the green compact of the insulation element is heat treated. This is already associated with some shrinkage of the volume of the insulation element green compact. But the volume of the green compact does not reach its final stage. Rather, another heat treatment as part of step d) is required, in which the insulation element green compact and the bearing element green compact shrink to their final size. In said development, the green compacts are heat treated only partly in order to already attain a certain surface hardness to render the handling of the green compact of the insulation element easier. This is expedient, for example, in the case of insulating compositions of materials which can be pressed only with some difficulty. In this context, the introduction of the bearing element green compact into the insulation element green compact might lead to destruction of the latter. To prevent this from occurring, the insulation element green compact is already partly sintered.

Another development is characterized in that the bearing element green compact is also already partly sintered in step b). As described above for the insulation element green compact, the bearing element green compact can also be sintered to some extent in order to attain a certain surface stability. It needs to be noted that the final, complete sintering in this development also does not occur until step d). Consequently, the bearing element green compact also attains its final size only in step d).

Another development of the method is characterized in that the method includes the following steps preceding step d):

producing at least one cermet-containing fringe green compact for a fringe;

introducing the at least one bearing element green compact into the insulation element green compact, and introducing the insulation element green compact into the fringe green compact;

whereby step d) includes:

d. firing the insulation element green compact and the at least one bearing element green compact and the fringe green compact to obtain an insulation element with at least one bearing element and a fringe.

The special feature of this procedural step is that, aside from the bearing element green compact and the insulation element green compact, the fringe green compact is also sintered in one step. All three green compacts are generated, then joined, and subsequently fired and/or sintered as a unit. In one development, the production of the at least one cermet-containing fringe green compact can include partial sintering. In this context, it is again provided that the fringe green compact is partly sintered in order to attain higher surface stability.

FIG. 1 illustrates, in an exemplary fashion, an implantable device 100, such as, for example, a cardiac pacemaker, with an electrical bushing 10 being integrated into the metallic housing thereof. The electrical bushing 10 is connected to the housing 110 of the implantable device 100 in a hermetically sealed manner, by means of welding. It is therefore advantageous in one embodiment for a holding element 20 of the electrical bushing 10 to include a metal that can be welded to the housing 110 both easily and reliably. The electrical bushing 10 serves to establish an electrical connection between the hermetically sealed interior of the medical device 100 and the exterior of said therapeutic device.

Accordingly, a conducting coil 120, which is indicated only schematically herein and is connected to an electrical stimulation electrode, can be attached to the electrical bushing 10. Stimulation electrodes of this type are used, for example, in heart muscles in order to conduct signals of the cardiac pacemaker to the muscle. In order to attain hermetic sealing, the conducting wire 30 is embedded into an insulation element 40. The insulation element 40 leads to the formation of a hermetic seal between the holding element 20 and the at least one conducting wire 30 in a through-opening 22 that is formed by the annulus-like holding element 20. The electrically insulating insulation element prevents short-circuiting between the electrically conductive elongated conducting wire 30 and the metallic housing 110 and/or the metallic holding element 20.

According to the prior art, it is known to build an insulation element and provide it with a bore hole into which an elongated conducting wire is to be inserted. For hermetic connection of the conducting wire to the insulation element, the prior art introduces a metallization into said bore hole which is subsequently used as a basis for soldering. In the process, fissures and gaps can arise through which, for example, moisture can penetrate into the interior of the housing 110. Moreover, this type of connecting the conducting wire to the insulation element is both inconvenient and expensive.

Figure 2:
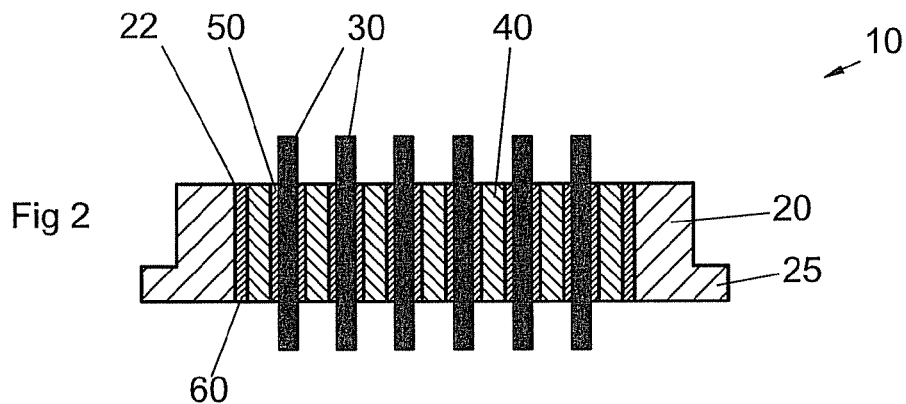
FIG. 2 illustrates a drawing of a section through an electrical bushing.
Figure 3:
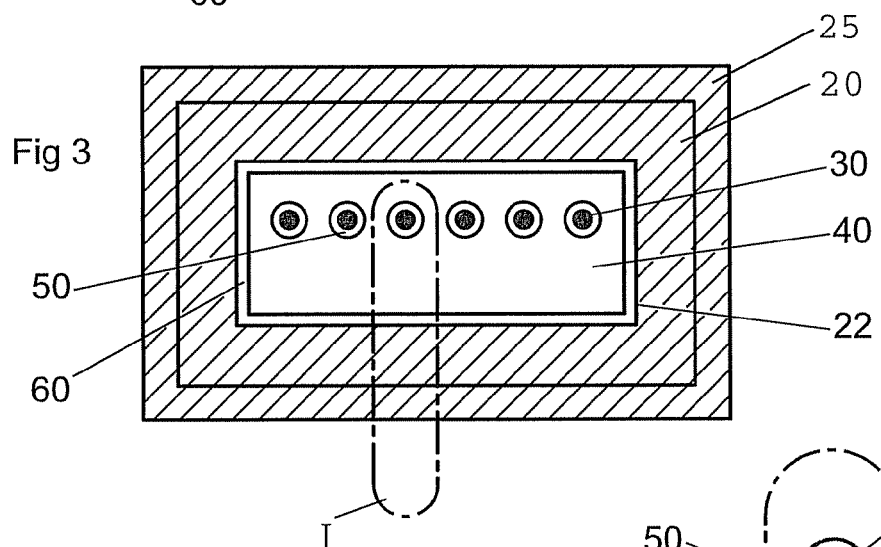
FIG. 3 illustrates a top view onto the electrical bushing.

In order to overcome said disadvantage, the electrical bushing according to one embodiment provides a cermet-containing bearing element 50 that is arranged between the insulation element 40 and the conducting wire 30. This is illustrated in FIG. 2. FIG. 2 illustrates a longitudinal section through an electrical bushing 10 that is designed according to one embodiment. The electrical bushing 10 includes the holding element 20, which is designed to be annulus-like and utilized to hold the electrical bushing 10 in the implantable medical device. The holding element 20 includes a through-opening 22. The insulation element 40 is arranged in said through-opening 22, as is illustrated for example, in FIG. 3 which illustrates a top view onto the electrical bushing 10 illustrated in FIG. 2.

In order to transport electrical pulses from the interior of the device 100 to an exterior of the device 100, the electrical bushing 10 includes a plurality of elongated conducting wires 30. Said conducting wires 30 extend through the insulation element 40. For connection of the insulation element 40 to the conducting wires 30, one embodiment provides each conducting wire 30 to be surrounded in a cuff-like manner by a cermet-containing bearing element 50. As illustrated, the cermet-containing bearing element 50 is designed to be tubular in shape and is of a length that is essentially equal to a height of the insulation element 40. Accordingly, there is no direct contact between the insulation element 40 and the conducting wire 30.

The following steps are performed in order to produce the electrical bushing 10 illustrated:
 a. generating an insulation element green compact for an insulation element (40) from an insulating composition of materials;
 b. forming at least one cermet-containing bearing element green compact for a bearing element (50);
 c. introducing the at least one bearing element green compact into the insulation element green compact;
 d. firing the insulation element green compact and the at least one bearing element green compact to obtain an insulation element (40) with at least one bearing element (50);
 e. inserting an elongated conducting wire (30) into the at least one bearing element (50); and
 f. surrounding, at least in part, the insulation element (40) with a holding element (20).

Due to both the bearing element 50 and the insulation element 40 being pressed from powders, in one embodiment it has proven to be advantageous to form both of them separately, to introduce the bearing element green compact into the insulation element green compact, and to sinter both of them jointly. This produces a connection between the two green compacts that is of the substance-to-substance- and/or non-positive fit- and/or positive fit-type.

Figure 4:
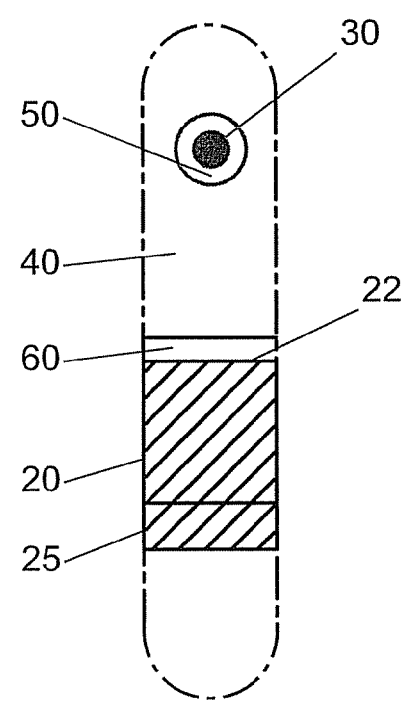
FIG. 4 illustrates a detail magnification of the electrical bushing.

FIG. 4 again illustrates the layered structure of the electrical bushing 10. This is a detail magnification of the region of FIG. 3 denoted I. The electrical bushing 10 includes an insulation element 40 that is to create a hermetic seal between the bearing element 50 and the holding element 20. In the exemplary embodiment illustrated, a cermet-containing fringe 60 is also arranged around the insulation element 40. Said cermet-containing fringe 60 can also be generated as a green compact and fired in one step jointly with the two aforementioned elements as part of the production of the bearing element 50 and insulation element 40. The cermet-containing bearing element 50 is designed to be cylindrical in shape and is incorporated inside the insulation element 40. Said bearing element 50 serves as bearing for the conducting wire 30. Appropriate welding or soldering procedures can be used to directly connect the conducting wire 30 to the bearing element in a substance-to-substance-type fit without any need for metallization of the interior of the bearing element 50.

The holding element 20 includes a flange 25 for integration of the electrical bushing 10 in the implantable medical device 100. In the development illustrated, the flange 25 is arranged in an L-shape on the holding element 20. A housing 110 of the device 100 can touch against the flange 25 in order to thus achieve a hermetically sealed connection between the two elements. In one embodiment, the holding element 20 and the flange 25 are made of the same material and/or in the form of a single part.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An electrical bushing for an implantable medical device comprising:
 an annulus-like holding element configured to hold the electrical bushing within the implantable medical device,
 wherein the holding element comprises a through-opening and at least one elongated conducting wire comprising metal extending through the through-opening and configured to transmit electrical signals between an inside and outside the implantable medical device;
 a first hermetic seal formed between the insulation element and the holding element arranged in the through-opening; wherein the insulation element further comprises a ceramic;
 a cermet-containing bearing element arranged between the insulation element and the conducting wire and configured to surround the conducting wire in a cuff-like manner thereby separating the conducting wire from the insulating element,
 wherein a second hermetic seal between the bearing element and the insulation element is formed and consists only of the bearing element and the insulation element which are introduced as green compacts and fired together thereby forming the second hermetic seal between the insulation element and the bearing element without metallization or solder therebetween.

2. The electrical bushing according to claim 1, characterized in that the bearing element separates the conducting wire from the insulation element in a cuff-like manner.

3. The electrical bushing according to claim 1, characterized in that a cermet-containing fringe is arranged between the insulation element and the holding element.

4. The electrical bushing according to claim 1, characterized in that the at least one elongated conducting wire comprises a metal from a group comprising Ti, Ta, Pt and an alloy of at least one of said metals.

5. The electrical bushing according to claim 1, characterized in that the insulation element is made from an insulating composition of materials, and in that the insulating composition of materials is at least one from a group comprising aluminum oxide, magnesium oxide, zirconium oxide, aluminum-titanate, and piezo-ceramics.

6. The electrical bushing according to claim 1, characterized in that the holding element comprises at least one flange, and in that the flange is conductive like a metal.

7. The electrical bushing according to claim 1, characterized in that the holding element and/or the at least one flange comprise a metal from a group comprising Ti, Ta, Pt and an alloy of at least one of said metals.

8. The electrical bushing according to claim 1, used in an electrical bushing for an implantable medical device.

9. An implantable medical device comprising:
an electrical bushing having an annulus-like holding element for holding the electrical bushing in the implantable medical device;
wherein the holding element comprises a through-opening and at least one elongated conducting wire comprising metal extending through the through-opening and configured to transmit electrical signals between an inside and outside the implantable medical device;
a first hermetic seal formed between the insulation element and the holding element arranged in the through-opening; wherein the insulation element further comprises a ceramic; wherein the insulation element defines a height;
a cermet-containing bearing element arranged between the insulation element and the conducting wire, the bearing element configured in a cylindrical shape that surrounds the conducting wire and separates the conducting wire from the insulation element along its entire I path through the insulation element; wherein a second hermetic seal between the bearing element and the insulation element is formed and consists only of the bearing element and the insulation element which are introduced as green compacts and fired together thereby forming a hermetic seal between them.

10. The implantable medical device of claim 9, wherein the medical device is one of a cardiac pacemaker and a defibrillator.

\* \* \* \* \*